United States Patent
Mito et al.

(10) Patent No.: US 7,205,260 B2
(45) Date of Patent: Apr. 17, 2007

(54) HERBICIDE COMPOSITION

(75) Inventors: Nobuaki Mito, Funabashi (JP); Shinsuke Shibuya, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 95 days.

(21) Appl. No.: 10/490,701

(22) PCT Filed: Apr. 26, 2002

(86) PCT No.: PCT/JP02/04194

§ 371 (c)(1), (2), (4) Date: Mar. 25, 2004

(87) PCT Pub. No.: WO03/028463

PCT Pub. Date: Apr. 10, 2003

(65) Prior Publication Data

US 2004/0235661 A1    Nov. 25, 2004

(30) Foreign Application Priority Data

Sep. 28, 2001 (JP) .............................. 2001-300862

(51) Int. Cl.
- *A01N 43/54* (2006.01)
- *A01N 43/48* (2006.01)
- *C07D 239/54* (2006.01)

(52) U.S. Cl. ................. 504/243; 504/168; 544/312; 544/314

(58) Field of Classification Search ................ 504/136, 504/225, 243, 273, 168; 544/312, 314

See application file for complete search history.

(56) References Cited

U.S. PATENT DOCUMENTS 5,990,044 A   11/1999  Santel et al.
6,451,740 B2   9/2002  Tohyama et al.

FOREIGN PATENT DOCUMENTS

| | | | |
|---|---|---|---|
| EP | 1 106 607 | * | 6/2001 |
| JP | 10-505072 A | | 5/1998 |
| JP | 2001-64266 A | | 3/2001 |
| JP | 2001-72668 A | | 3/2001 |
| JP | 2001-354661 A | | 12/2001 |
| JP | 2002-53560 A | | 2/2002 |
| WO | WO 98/41093 A1 | | 9/1998 |
| WO | WO 00/02866 A1 | | 1/2000 |
| WO | WO 01/39597 A2 | | 6/2001 |
| WO | WO 02/098227 A1 | | 12/2002 |

* cited by examiner

*Primary Examiner*—Johann Richter
*Assistant Examiner*—Mina Haghighatian
(74) *Attorney, Agent, or Firm*—Sughrue Mion, PLLC

(57) ABSTRACT

The present invention relates to an herbicide composition comprising, as active ingredients, a uracil compound represented by the following formula (I):

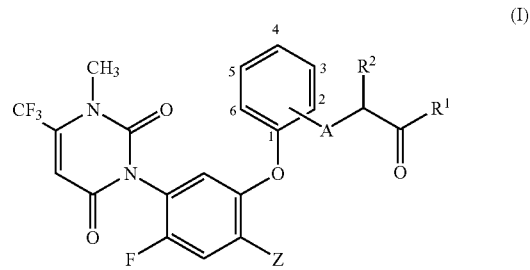

wherein Z represents halogen or cyano; A represents oxygen, sulfur or NH; $R^1$ represents hydroxyl, C1–C7 alkoxy or others, and $R^2$ represents hydrogen or methyl, and one or more compounds selected from the group consisting of N-(7-fluoro-3,4-dihydro-3-oxo-4-prop-2-ynyl-2H-1,4-benzoxazin-6-yl)cyclohex-1-ene-1,2-dicarboxamide and N-[2,4-dichloro-5-[4-(difluoromethyl)-4,5-dihydro-3-methyl-5-oxo-1H-1,2,4-triazol-1-yl]phenyl]methanesulfonamide; and a method for controlling weeds which comprises applying an effective amounts of said herbicide composition to weeds.

According to the invention, particularly weeds in orchards, soybean fields and non-crop lands can be effectively controlled.

6 Claims, No Drawings

HERBICIDE COMPOSITION

TECHNICAL FIELD

The present invention relates to an herbicide composition, particularly to an herbicide composition suitable to control weeds in orchards, soybean fields and non-crop lands.

BACKGROUND ART

While numerous herbicides are currently marketed and used, weeds to be controlled are varied in kind and their emergence continues over a long term. Herbicides with a higher activity and a broader spectrum of weeds and without a phytotoxicity problem on crops have been demanded.

DISCLOSURE OF THE INVENTION

As a result of extensive studies searching for an excellent herbicide, the present inventor has found facts that a combined use of a uracil compound (hereinafter referred to as the present uracil compound) represented by the following formula (I):

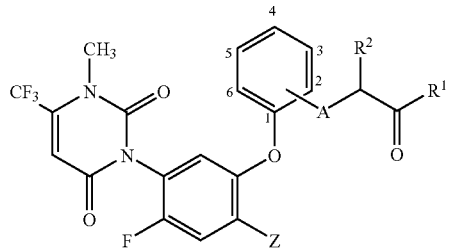

(I)

wherein Z represents a halogen atom or cyano; A represents an oxygen atom, sulfur atom or NH; $R^1$ represents hydroxyl, C1–C7 alkoxy, C3–C7 alkenyloxy, C3–C7 alkynyloxy, C5–C7 cycloalkoxy, {(C1–C7 alkoxy)carbonyl}C1–C3 alkoxy, (C1–C7 alkylamino)oxy, {di(C1–C7 alkyl)amino}oxy, (C3–C7 alkylideneamino)oxy, C1–C7 alkylamino, di(C1–C7 alkyl)amino, C3–C7 alkenylamino, C3–C7 alkynylamino, C5–C7 cycloalkylamino, {(C1–C7 alkoxy)carbonyl}C1–C3 alkylamino or (C1–C7 alkoxy)amino, and $R^2$ represents a hydrogen atom or methyl, and one or more heterocyclic compounds (hereinafter referred to as the present heterocyclic compound), which inhibit protoporphyrinogen oxidase (Protox), selected from the group consisting of N-(7-fluoro-3,4-dihydro-3-oxo-4-prop-2-ynyl-2H-1,4-benzoxazin-6-yl)cyclohex-1-ene-1,2-dicarboxamide (generic name: flumioxazin; hereinafter referred to as Flumioxazin) and N-[2,4-dichloro-5-[4-(difluoromethyl)-4,5-dihydro-3-methyl-5-oxo-1H-1,2,4-triazol-1-yl]phenyl]methanesulfonamide (generic name: sulfentrazone; hereinafter referred to as Sulfentrazone) can effective control various weeds and that the herbicidal effect with the combined use is synergistically increases when compared with single uses of them, and thus they completed the present invention. When a composition comprising the present uracil compound and the present heterocyclic compounds is used as an herbicide, the application can be carried out at a lowered dose, the herbicidal spectrum can be broadened, and particularly, a wide variety of weeds can be controlled in orchards and soybean fields.

Therefore, the invention provides:
1. an herbicide composition (hereinafter referred to as the present composition) comprising, as the active ingredients, the present uracil compound and the present heterocyclic compound;
2. the herbicide composition according to above 1, wherein, in the present uracil compound, A is an oxygen atom and $R^1$ is C1–C7 alkoxy;
3. the herbicide composition according to above 1, wherein, in the present uracil compound, the substituent represented by the following formula:

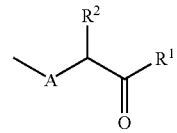

wherein $R^1$, $R^2$ and A represent the same meaning as above, is attached to the 2-position as defined in the formula (I);
4. the herbicide composition according to above 1, wherein, in the present uracil compound, the substituent represented by the following formula:

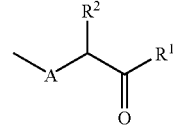

wherein $R^1$, $R^2$ and A represent the same meaning as above, is attached to the 3-position or 4-position as defined in the formula (I);
5. the herbicide composition according to above 1, wherein, in the present uracil compound, Z is a halogen atom and $R^2$ is a hydrogen atom;
6. the herbicide composition according to above 1, wherein, in the present uracil compound, Z is cyano;
7. the herbicide composition according to above 1, wherein the mixing ratio of the present uracil compound to the present heterocyclic compound is 1:0.5 to 1:300 in weight ratio;
8. a method for controlling weeds (hereinafter referred to as the present method) comprising applying effective amounts of the present uracil compound and the present heterocyclic compound to weeds;
9. the method for controlling weeds according to above 8, wherein the weeds are weeds in an orchard;
10. the method for controlling weeds according to above 8, wherein the weeds are weeds in a soybean field;
11. the method for controlling weeds according to above 8, wherein the weeds are weeds in a non-crop land;
12. a use of a composition comprising the present uracil compound and the present heterocyclic compound as an herbicide;
13. the use according to above 12, wherein the herbicide is an herbicide for an orchard;
14. the use according to above 12, wherein the herbicide is an herbicide for a soybean field;
15. the use according to above 12, wherein the herbicide is an herbicide for a non-crop land.

In the present invention, a halogen atom represented by Z in the formula (I) means a fluorine atom, chlorine atom, bromine atom or iodine atom; C1–C7 alkoxy represented by R¹ includes methoxy, ethoxy, propoxy, isopropoxy, butoxy, 1-methylpropoxy, 2-methylpropoxy, pentyloxy, 1-methylbutoxy, 2-methylbutoxy, 3-methylbutoxy, 2,2-dimethylpropoxy, hexyloxy, 1-methylpentyloxy, 2-methylpentyloxy, 3-methylpentyloxy, 4-methylpentyloxy, 1,2-dimethylbutoxy, 1,3-dimethylbutoxy, 2,3-dimethylbutoxy, 3,3-dimethylbutoxy, heptyloxy and the like; C3–C7 alkenyloxy represented by R¹ includes 2-propynyloxy, 3-butenyloxy, 4-pentenyloxy, 3-methyl-3-butenyloxy, 3-methyl-2-butenyloxy and the like; C3–C7 alkynyloxy represented by R¹ includes 2-propynyloxy and the like; C5–C7 cycloalkoxy represented by R¹ includes cyclopentyloxy, cyclohexyloxy and the like; {(C1–C7 alkoxy)carbonyl} C1–C3 alkoxy represented by R¹ includes methoxycarbonylmethoxy, ethoxycarbonylmethoxy, 1-(methoxycarbonyl)-1-methylethoxy and the like; (C1–C7 alkylamino)oxy represented by R¹ includes (methylamino)oxy, (ethylamino)oxy and the like; {di(C1–C7 alkyl)amino}oxy represented by R¹ includes (dimethylamino)oxy, (methylethylamino)oxy and the like; (C3–C7 alkylideneamino)oxy represented by R¹ (isopropylideneamino)oxy and the like; C1–C7 alkylamino represented by R¹ includes methylamino, ethylamino, propylamino, isopropylamino, butylamino, 1-methylpropylamino, 2-methylpropylamino, pentylamino, 1-methylbutylamino, 2-methylbutylamino, 3-methylbutylamino, 2,2-dimethylpropylamino, hexylamino and the like; di(C1–C7 alkyl)amino represented by R¹ includes dimethylamino, diethylamino and the like; C3–C7 alkenylamino represented by R¹ includes 2-propenylamino and the like; C3–C7 alkynylamino represented by R¹ includes 2-propynylamino and the like; C5–C7 cycloalkylamino represented by R¹ includes cyclopentylamino, cyclohexylamino and the like; {(C1–C7 alkoxy) carbonyl} C1–C3 alkylamino represented by R¹ includes methoxycarbonylmethylamino and the like; (C1–C7 alkoxy)amino represented by R¹ includes methoxyamino, ethoxyamino, isopropoxyamino and the like.

Flumioxazin and Sulfentrazone are compounds described in FARM CHEMICALS HANDBOOK 2001 (published by MEISTER PUBLISHING COMPANY in 2001), pages C374 and C35, respectively, and compounds which inhibit protoporphyrinogen oxidase (Protox). Flumioxazin and Sulfentrazone can be prepared by known processes; said compounds or formulations thereof are commercially available.

The present composition is excellent as an herbicide because it has an herbicide activity against a wide variety of weeds, and exhibits an excellent herbicide activity in ordinary crop lands such as plowing cultivation crop fields, non-tilled cropping fields, orchards and the like, and non-crop land such as sports grounds, vacant lands, forest lands, railroad sides and the like. The present composition is particularly effective in controlling a wide variety of weeds emerging in orchards, and does not cause troublesome phytotoxicity in fruit trees. In addition, the present composition is particularly effective in controlling a wide variety of weeds emerging in soybean fields from winter season to spring season before seeding of soybean, and does not cause troublesome phytotoxicity in seeded soybean after treatment.

The present composition has especially an herbicide activity against various weeds, listed below, causing trouble in orchards, soybean fields, non-crop land and the like.

Polygonaceae weeds: wild buckwheat (*Polygonum convolvulus*), pale smartweed (*Polygonum lapathifolium*), Pensylvania smartweed (*Polygonum pensylvanicum*), ladysthumb (*Polygonum persicaria*), curly dock (*Rumex crispus*), bitter dock(*Rumex obtusifolius*), Japanese knotweed (*Polygonum cuspidatum*).

Portulaceae weeds: common purslane (*Portulaca oleracea*).

Caryophyllaceae weeds: common chickweed (*Stellaria media*).

Chenopodiaceae weeds: common lambsquarters (*Chenopodium album*), summer cypress (*Kochia scoparia*).

Amaranthaceae weeds: redroot pigweed (*Amaranthus retroflexus*), smooth pigweed (*Amaranthus hybridus*).

Cruciferae weeds: wild radish (*Raphanus raphanistrum*), wild mustard (*Sinapis arvensis*), shepherds purse (*Capsella bursa-pastoris*).

Legminosae weeds: hemp sesbania (*Sesbania exaltata*), sickle pod (*Cassia obtusifolia*), Florida beggarweed (*Desmodium tortuosum*), white clover (*Trifolium repens*).

Malvaceae weeds: velvetleaf (*Abutilon theophrasti*), pricky sida (*Sida spinosa*).

Violaceae weeds: field pansy (*Viola arvensis*), wildpansy (*Viola tricolor*).

Rubiaceae weeds: bedstraw (*Galium aparine*).

Convolvulaceae weeds: ivyleaf morningglory (*Ipomoea hederacea*), tall morningglory (*Ipomoea purpurea*), entireleaf morningglory (*Ipomoea hederacea* var *integriuscula*), whitestar (*Ipomoea lacunosa*), field bindweed (*Convolvulus arvensis*).

Labiatae weeds: purple deadnettle (*Lamium purpureum*), henbit (*Lamium amplexicaule*).

Solanaceae weeds: jimsonweed (*Datura stramonium*), black nightshade (*Solanum nigrum*).

Scrophulariaceae weeds: persian speedwell (*Veronica persica*), ivyleaf speedwell (*Veronica hederaefolia*).

Compositae weeds: common cocklebur (*Xanthium pensylvanicum*), wild sunflower (*Helianthus annuus*), scentless chamomile (*Matricaria perforata* or *inodora*), corn marigold (*Chrysanthemum segetum*), pineapple weed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*).

Boraginaceae weeds: forget-me-not (*Myosotis arvensis*).

Asslepiadaceae weeds: milkweed (*Asclepias syriaca*).

Euphorbiaceae weeds: sun spurge (*Euphorbia helioscopia*), spurge (*Euphorbia maculata*).

Gramineae weeds: barnyard grass (*Echinochloa crusgalli*), green foxtail (*Setaria viridis*), giant foxtail (*Setaria faberi*), southern crabgrass (*Digitaria sanguinalis*), goose grass (*Eleusine indica*), annual bluegrass (*Poa annua*), black grass (*Alopecurus myosuroides*), wild oats (Avena fatua), Johnson grass (*Sorghum halepense*), quack grass (*Agropyron repens*), downy brome (*Bromus tectorum*), Bermuda grass (*Cynodone dactylon*), fall panicum (*Panicum dichotomiflorum*), Texas panicum (*Panicum texanum*), shatter cane (*Sorghum vulgare*), broadleaf signalgrass (*Brachiaria platyphylla*).

Commelinaceae weeds: asiatic dayflower (*Commelina communis*).

Equisetaceae weeds: field horsetail (*Equisetum arvense*).

Cryperaceae weeds: rice flatsedge (*Cyperus iria*), purple nutsedge (*Cyperus rotundus*), yellownutsedge (*Cyperus esculentus*).

In the present composition, the mixing ratio of the uracil compound to the present heterocyclic compound may vary depending on targeted kind of weeds, application locus, application conditions and the like, and usually it is a ratio showing a synergistic effect, specifically 1:0.1 to 1:500, preferably 1:0.5 to 1:300, and more preferably 1:1 to 1:300.

The present composition may contain other ingredients in addition to the present uracil compound and the present heterocyclic compound, and it is usually in the form of a formulation such as emulsion, wettable powder, suspension, granule and the like obtainable by mixing the present uracil compound and the present heterocyclic compound as the active ingredients together with a solid carrier, liquid carrier or the like and, if necessary, adding a surfactant, other formulation auxiliaries and the like. These formulations contain usually 0.5 to 90% by weight, preferably 1 to 80% by weight in total of the present uracil compound and the present heterocyclic compound.

In formulation, usable solid carriers include, for example, fine powders and granules such as clays (kaolinite, diatomaceous earth, synthetic hydrous silicon oxide, Fubasami clay, bentonite, acidclayandthelike), talc, other inorganic minerals (sericite, quarts powder, sulfur powder, activated carbon, calcium carbonate and the like), chemical fertilizers (ammonium sulfate, ammonium phosphate, ammonium nitrate, ammonium chloride, urea and the like) and so on; and liquid carriers include, for example, water, alcohols (methanol, ethanol and the like), ketones (acetone, methyl ethyl ketone, cyclohexanone and the like), aromatic hydrocarbons (toluene, xylene, ethylbenzene, methylnaphthalene and the like), non-aromatic hydrocarbons (hexane, cyclohexane, kerosene and the like), esters (ethyl acetate, butyl acetate and the like), nitriles (acetonitrile, isobutyronitrile and the like), ethers (dioxane, diisopropyl ether and the like), acid amides (dimethylformamide, dimethylacetamide and the like), halogenated hydrocarbons (dichloroethane, trichloroethylene and the like) and so on.

Surfactants include, for example, alkyl sulfate esters, alkyl sulfonate salts, alkyl aryl sulfonate salts, alkyl aryl ethers and their polyoxyethylene compounds, polyoxyethylene glycol ethers, polyhydric alcohol esters, sugar alcohol derivatives and the like.

Other formulation auxiliaries include, for example, sticking agents and dispersing agents such as casein, gelatin, polysaccharides (starch, gum Arabic, cellulose derivatives, alginic acid and the like), lignin derivatives, bentonite, synthetic water-soluble high molecules (polyvinyl alcohol, polyvinyl pyrrolidone, polyacrylic acid and the like) and the like, stabilizing agents such as PAP (acidic isopropyl phosphate), BHT (2,6-tert-butyl-4-methylphenol), BHA (2-/3-tert-butyl-4-methoxyphenol), vegetable oils, mineral oils, fatty acids, fatty acid esters and the like.

The present composition can also be obtained by separately formulating the present uracil compound and the present heterocyclic compound as the active ingredients according to the above described formulation process and then mixing both of the formulations.

The present composition is applied as it is or, if necessary, after dilution onto leaves and stems of weeds. Sometimes, enhancement of herbicide activity can be expected by using the present composition with another herbicide. In addition, it may be concurrently used together with an insecticide, fungicide, plant growth regulator, phytotoxicity reducing agent (safener) and the like.

Amount to be applied of the present composition may vary depending on the mixing ratio of the present uracil compound to the present heterocyclic compound as the active ingredients, meteorological conditions, formulation forms, time of application, method of application, locus of application, a kind of weed to be controlled, a kind of crop to be protected and the like; the total amount of the present uracil compound and the present heterocyclic compound per hectare is usually 10 g to 2,000 g, preferably 20 g to 1,500 g. Emulsions, wettable powders, suspensions and the like of the present composition are applied in a predetermined amount usually diluted with 100 to 1,000 liters of water per hectare. Enhancement of the effect to weeds can be expected by adding adjuvant to aqueous diluent.

The present method is usually carried out by applying an effective amount of the present composition to weeds; it can also be carried out by applying effective amounts of the present uracil compound and the present heterocyclic compound independently but at the same stage according to the above described amount, manner of use and the like.

Some examples of the present uracil compound are specifically described in the following.

Compounds represented by the formula (I-a):

TABLE 1

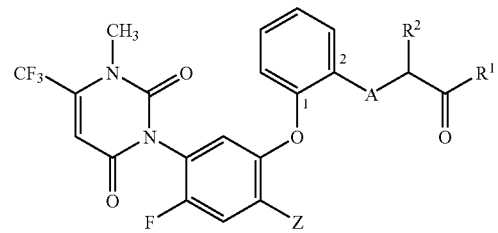

(I-a)

| Compound No. | A | Z | $R^2$ | $R^1$ |
|---|---|---|---|---|
| A-1 | O | Cl | H | $OCH_3$ |
| A-2 | O | Cl | H | $OC_2H_5$ |
| A-3 | O | Cl | $CH_3$ | $OCH_3$ |
| A-4 | O | Cl | $CH_3$ | $OC_2H_5$ |
| A-5 | O | CN | H | $OCH_3$ |
| A-6 | O | CN | $CH_3$ | $OC_2H_5$ |
| A-7 | O | Br | H | $OCH_3$ |

Compounds represented by the formula (I-b):

TABLE 2

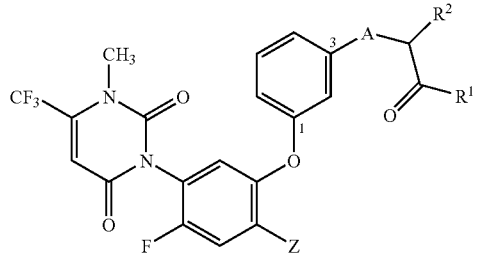

(I-b)

| Compound No. | A | Z | $R^2$ | $R^1$ |
|---|---|---|---|---|
| B-1 | O | Cl | H | $OCH_3$ |
| B-2 | O | Cl | $CH_3$ | $OCH_3$ |
| B-3 | O | CN | H | $OCH_3$ |
| B-4 | O | CN | $CH_3$ | $OC_2H_5$ |

Compounds represented by the formula (I-c):

TABLE 3

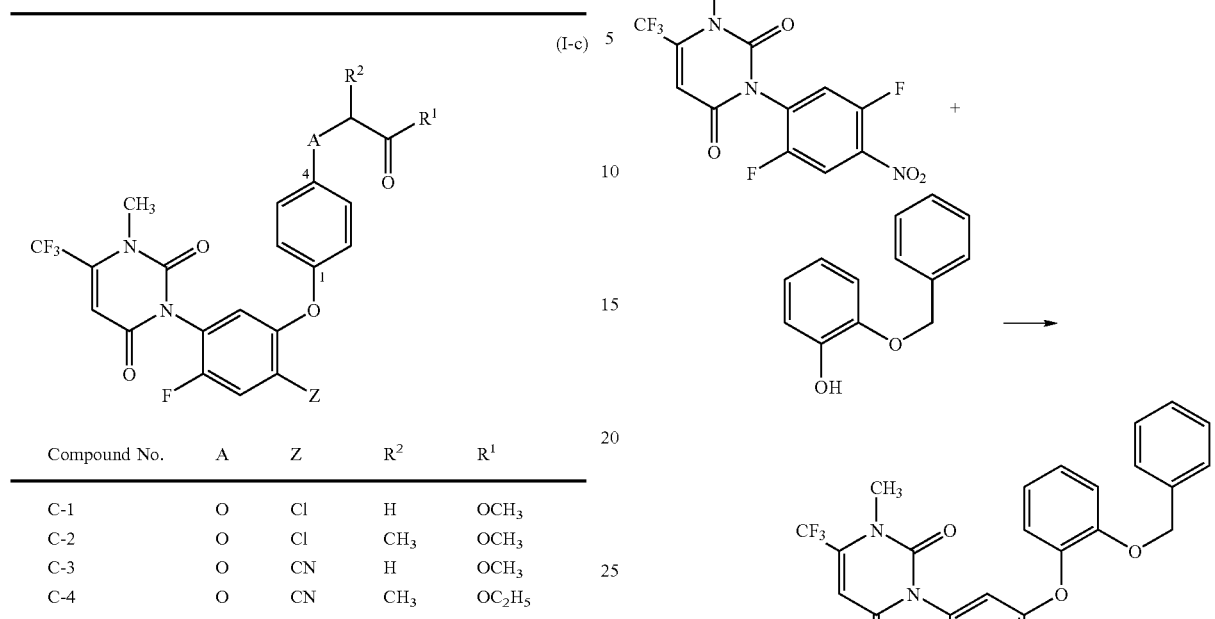

| Compound No. | A | Z | R² | R¹ |
|---|---|---|---|---|
| C-1 | O | Cl | H | OCH₃ |
| C-2 | O | Cl | CH₃ | OCH₃ |
| C-3 | O | CN | H | OCH₃ |
| C-4 | O | CN | CH₃ | OC₂H₅ |

The present uracil compounds can be produced, for example, according to the process described in EP 1,106,607. For example, Compound A-3 can be produced by the following process:

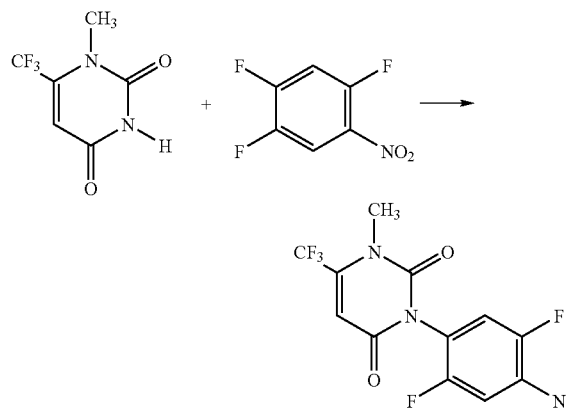

Into 10 ml of dimethylsulfoxide was dissolved 1.77 g of 2,4,5-trifluoronitrobenzene and 1.94 g of 3-methyl-2,6-dioxo-4-(trifluoromethyl)-1,2,3,6-tetrahydro pyrimidine. After adding 1.52 g of anhydrous potassium carbonate at room temperature, the mixture was stirred at 80° C. for 1 hour. The reaction solution was cooled to room temperature, and then the solution was poured into ice-water and extracted with ethyl acetate. The organic layer was washed with saturated aqueous sodium chloride solution, dried over anhydrous magnesium sulfate and concentrated. The residue was subjected to silica-gel column chromatography to give 1.51 g of 2,5-difluoro-4-[3-methyl-2,6-dioxo-4-(trifluoromethyl)-1,2,3,6-tetrahydropyrimidin-1-yl]nitrobenzene.

Mp: 150° C.

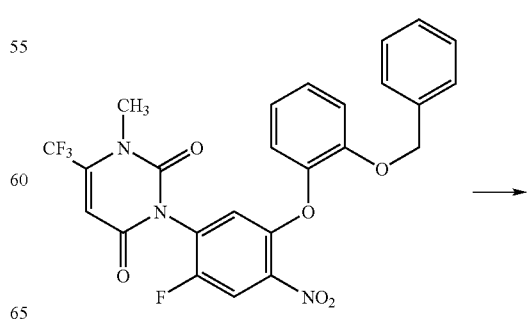

A mixture of 4.05 g of 2-benzyloxyphenol and 9.5 ml of N,N-dimethylformamide was added dropwise to a mixture of 0.80 g of sodium hydride and 20 ml of N,N-dimethylformamide under ice cooling and the mixture was stirred for 30 minutes. A mixture of 7.1 g of 2,5-difluoro-4-[3-methyl-2,6-dioxo-4-(trifluoromethyl)-1,2,3,6-tetrahydropyrimidin-1-yl]nitrobenzene and 17 ml of N,N-dimethylformamide was added dropwise at the same temperature and the mixture was stirred for 1 hour. The reaction solution was poured into ice-water and extracted with ethyl acetate. The organic layer was washed successively once with 1N—HCl and once with saturated aqueous sodium chloride solution, dried over anhydrous magnesium sulfate and concentrated. The residue was subjected to silica-gel column chromatography to give 8.6 g of 2-(2-benzyloxyphenoxy)-5-fluoro-4-[3-methyl-2,6-dioxo-4-(trifluoromethyl)-1,2,3,6-tetrahydropyrimidin-1-yl]nitrobenzene.

¹H-NMR (CDCl₃/250 MHz), δ (ppm): 3.52 (q,3H, J=1.1 Hz), 5.01 (s,2H), 6.31 (s,1H), 6.81 (d,1H, J=6.0 Hz), 6.9–7.1 (m,2H), 7.1–7.4 (m,7H), 7.78 (d,1H, J=8.7 Hz).

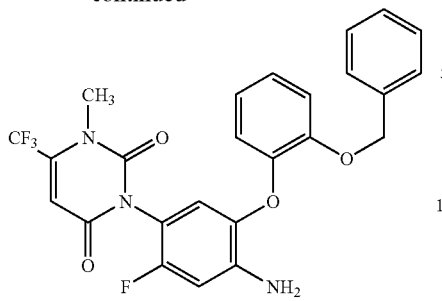

To a mixture of 8.6 g of iron powder, 27 ml of acetic acid and 2.7 ml of water was added dropwise a solution of 8.6 g of 2-(2-benzyloxyphenoxy)-5-fluoro-4-[3-methyl-2,6-dioxo-4-(trifluoromethyl)-1,2,3,6-tetrahydropyrimidin-1-yl]nitrobenzene in 23 ml of acetic acid while keeping the temperature of the reaction solution at or below 35° C. After the addition was finished, the stirring was continued for 2 hours and then the reaction solution was filtered through celite and diluted with ethyl acetate. The mixture was neutralized with saturated aqueous sodium hydrogen carbonate solution and the organic layer was washed with saturated aqueous sodium chloride solution, dried over anhydrous magnesium sulfate and concentrated. The obtained residue was subjected to silica-gel column chromatography to give 6.46 g of 2-(2-benzyloxyphenoxy)-5-fluoro-4-[3-methyl-2,6-dioxo-4-(trifluoromethyl)-1,2,3,6-tetrahydropyrimidin-1-yl]aniline.

$^1$H-NMR (CDCl$_3$/250 MHz), δ (ppm): 3.50 (q,3H,J=1.2 Hz), 5.06 (s,2H), 6.29 (s,1H), 6.57 (dd,1H, J=8.5, 1.6 Hz), 6.9–7.0 (m,1H), 7.0–7.1 (m,3H), 7.2–7.4 (m,6H).

To a mixture of 6.46 g of 2-(2-benzyloxyphenoxy)-5-fluoro-4-[3-methyl-2,6-dioxo-4-(trifluoromethyl)-1,2,3,6-tetrahydropyrimidin-1-yl]aniline, 2.45 g of copper chloride (I), 5.04 g of copper chloride (II) and 90 ml of acetonitrile was added dropwise 4.46 g of isoamyl nitrite at room temperature, and the mixture was stirred for 1 hour. The reaction solution was poured into 2% hydrochloric acid and extracted with ethyl acetate. The organic layer was washed with saturated aqueous sodium chloride solution, dried over anhydrous magnesium sulfate and concentrated. The obtained residue was subjected to silica-gel column chromatography to give 4.6 g of ([2-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene.

Mp: 50.8° C.

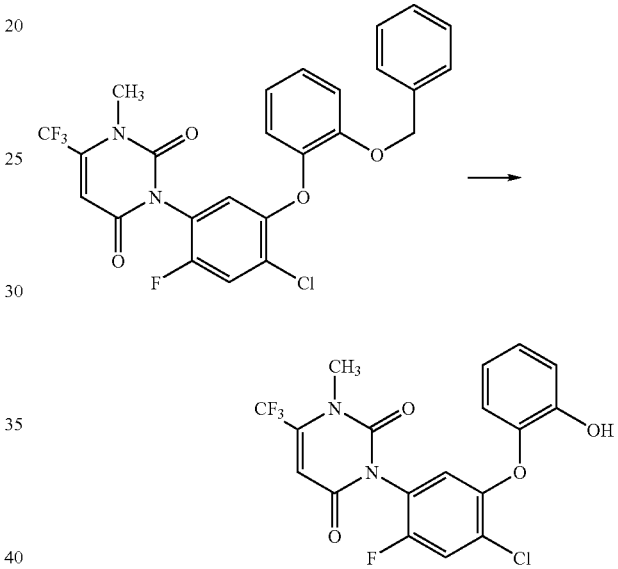

To 4.5 g of ([2-{2-chloro-4-fluoro-5-[3-methyl-2,6-dioxo-4-(trifluoromethyl)-1,2,3,6-tetrahydropyrimidin-1-yl]phenoxy}phenoxy]methyl)benzene were added 230 ml of ethyl acetate and 0.46 g of 10% palladium-on-carbon, and the mixture was stirred under hydrogen atmosphere at room temperature for 5 hours. After replacing the reaction system by nitrogen, the reaction solution was filtered over celite and the filtrate was concentrated to give 3.57 g of 2-{2-chloro-4-fluoro-5-[3-methyl-2,6-dioxo-4-(trifluoromethyl)-1,2,3,6-tetrahydropyrimidin-1-yl]phenoxy}phenol.

Mp: 55.4° C.

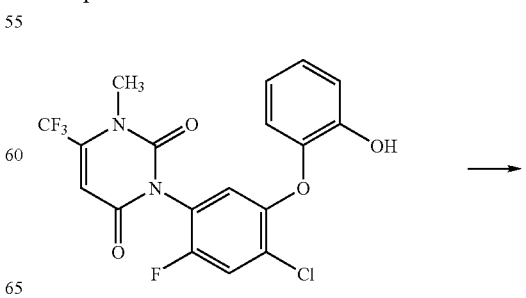

-continued

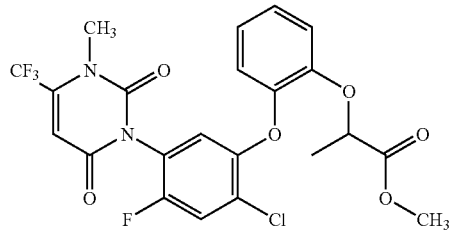

Into 6 ml of N,N-dimethylformamide was dissolved 0.23 g of 2-{2-chloro-4-fluoro-5-[3-methyl-2,6-dioxo-4-(trifluoromethyl)-1,2,3,6-tetrahydropyrimidin-1-yl]phenoxy}phenol. After adding 0.22 g of anhydrous potassium carbonate, 0.13 g of methyl 2-bromopropionate was added at room temperature with stirring and then the mixture was stirred at 80° C. for 3 hours. After cooling the reaction solution to room temperature, the reaction solution was poured into ice-water and extracted with ethyl acetate. The organic layer was washed with saturated aqueous sodium chloride solution, dried over anhydrous magnesium sulfate and concentrated. The residue was subjected to silica-gel column chromatography to give 0.23 g of methyl 2-[2-{2-chloro-4-fluoro-5-[3-methyl-2,6-dioxo-4-(trifluoromethyl)-1,2,3,6-tetrahydropyrimidin-1-yl]phenoxy}phenoxy]propionate [Compound A-3].

$^1$H-NMR (CDCl$_3$/250 MHz) δ (ppm): 1.47 (d,3H, J=6.8 Hz), 3.50 (q,3H, J=0.7 Hz), 3.6–3.8 (m,3H), 4.6–4.8 (m,1H), 6.28 (s,1H), 6.7–6.8 (m,1H), 6.8–6.9 (m,1H), 6.9–7.1 (m,1H), 7.1–7.2 (m,2H), 7.3–7.4 (m,1H).

Formulation examples are shown in the following. In the following formulation examples and test examples, compounds represented by compound numbers are the compounds in Table 1 to 3 and part means part by weight.

FORMULATION EXAMPLE 1

Each of wettable powders is obtained by sufficiently pulverizing and mixing 15 parts of Compound A-1, A-2, A-3, A-4, A-5, A-6, A-7, B-1, B-2, B-3, B-4, C-1, C-2, C-3 or C-4, 75 parts of Flumioxazin, 3 parts of calcium ligninsulfonate, 2 parts of sodium lauryl sulfate, and 10 parts of synthetic hydrous silicon oxide.

FORMULATION EXAMPLE 2

Each of wettable powders is obtained by sufficiently pulverizing and mixing 0.8 part of Compound A-1, A-2, A-3, A-4, A-5, A-6, A-7, B-1, B-2, B-3, B-4, C-1, C-2, C-3 or C-4, 80 parts of Flumioxazin, 3 parts of calcium ligninsulfonate, 2 parts of sodium lauryl sulfate, and 14.2 parts of synthetic hydrous silicon oxide.

FORMULATION EXAMPLE 3

Each of wettable powders is obtained by sufficiently pulverizing and mixing 20 parts of Compound A-1, A-2, A-3, A-4, A-5, A-6, A-7, B-1, B-2, B-3, B-4, C-1, C-2, C-3 or C-4, 20 parts of Flumioxazin, 3 parts of calcium ligninsulfonate, 2 parts of sodium lauryl sulfate, and 55 parts of synthetic hydrous silicon oxide.

FORMULATION EXAMPLE 4

Each of wettable powders is obtained by sufficiently pulverizing and mixing 8 parts of Compound A-1, A-2, A-3, A-4, A-5, A-6, A-7, B-1, B-2, B-3, B-4, C-1, C-2, C-3 or C-4, 80 parts of Sulfentrazone, 3 parts of calcium ligninsulfonate, 2 parts of sodium lauryl sulfate, and 7 parts of synthetic hydrous silicon oxide.

FORMULATION EXAMPLE 5

Each of wettable powders is obtained by sufficiently pulverizing and mixing 0.4 parts of Compound A-1, A-2, A-3, A-4, A-5, A-6, A-7, B-1, B-2, B-3, B-4, C-1, C-2, C-3 or C-4, 80 parts of Sulfentrazone, 3 parts of calcium ligninsulfonate, 2 parts of sodium lauryl sulfate, and 14.6 parts of synthetic hydrous silicon oxide.

FORMULATION EXAMPLE 6

Each of wettable powders is obtained by sufficiently pulverizing and mixing 10 parts of Compound A-1, A-2, A-3, A-4, A-5, A-6, A-7, B-1, B-2, B-3, B-4, C-1, C-2, C-3 or C-4, 20 parts of Sulfentrazone, 3 parts of calcium ligninsulfonate, 2 parts of sodium lauryl sulfate, and 14.6 parts of synthetic hydrous silicon oxide.

FORMULATION EXAMPLE 7

Each of suspensions is obtained by wet-grinding 8 parts of Compound A-1, A-2, A-3, A-4, A-5, A-6, A-7, B-1, B-2, B-3, B-4, C-1, C-2, C-3 or C-4, 40 parts of Flumioxazin, 3 parts of polyoxyethylene sorbitan monooleate, 3 parts of CMC (carboxymethylcellulose), and 46 parts of water; and wet-grinding until the particle size was 5 micron or lower.

FORMULATION EXAMPLE 8

Each of suspensions is obtained by wet-grinding 0.4 part of Compound A-1, A-2, A-3, A-4, A-5, A-6, A-7, B-1, B-2, B-3, B-4, C-1, C-2, C-3 or C-4, 40 parts of Flumioxazin, 3 parts of polyoxyethylene sorbitan monooleate, 3 parts of CMC (carboxymethylcellulose), and 53.6 parts of water; and wet-grinding until the particle size was 5 micron or lower.

FORMULATION EXAMPLE 9

Each of suspensions is obtained by wet-grinding 5 parts of Compound A-1, A-2, A-3, A-4, A-5, A-6, A-7, B-1, B-2, B-3, B-4, C-1, C-2, C-3 or C-4, 5 parts of Flumioxazin, 3 parts of polyoxyethylene sorbitan monooleate, 3 parts of CMC (carboxymethylcellulose), and 84 parts of water; and wet-grinding until the particle size was 5 micron or lower.

FORMULATION EXAMPLE 10

Each of suspensions is obtained by wet-grinding 4 parts of Compound A-1, A-2, A-3, A-4, A-5, A-6, A-7, B-1, B-2, B-3, B-4, C-1, C-2, C-3 or C-4, 40 parts of Glufosinate-Ammonium, 3 parts of polyoxyethylene sorbitan monooleate, 3 parts of CMC (carboxymethylcellulose), and 50 parts of water; and wet-grinding until the particle size was 5 micron or lower.

FORMULATION EXAMPLE 11

Each of suspensions is obtained by wet-grinding 0.2 part of Compound A-1, A-2, A-3, A-4, A-5, A-6, A-7, B-1, B-2, B-3, B-4, C-1, C-2, C-3 or C-4, 40 parts of Sulfentrazone, 3 parts of polyoxyethylene sorbitan monooleate, 3 parts of CMC (carboxymethylcellulose), and 53.8 parts of water; and wet-grinding until the particle size was 5 micron or lower.

FORMULATION EXAMPLE 12

Each of suspensions is obtained by wet-grinding 5 parts of Compound A-1, A-2, A-3, A-4, A-5, A-6, A-7, B-1, B-2, B-3, B-4, C-1, C-2, C-3 or C-4, 10 parts of Sulfentrazone, 3 parts of polyoxyethylene sorbitan monooleate, 3 parts of CMC (carboxymethylcellulose), and 79 parts of water; and wet-grinding until the particle size was 5 micron or lower.

Test examples are shown in the following.

Evaluation Criterions:

Evaluation of the herbicide activity is divided into 11 levels and shown by 0, 1, 2, 3, 4, 5, 6, 7, 8, 9 or 10, wherein a level was taken "0" when completely or almost no difference was observed between the growth behavior of a test weed at the time of observation and that of untreated weed and a level was taken "10" when a test weed completely died or the growth of that was completely inhibited. Evaluation of phytotoxicity against a crop was shown by "no" when almost no phytotoxicity was observed, "low" when a low level phytotoxicity was observed, "medium" when a medium level phytotoxicity was observed and "high" when a high level phytotoxicity was observed.

TEST EXAMPLE 1

A plastic pot of 11 cm in diameter and 8 cm in depth was filled with field soil. A seed of broadleaf signalgrass was sown and grown in a greenhouse for 28 days.

An emulsion of Compound A-1 was prepared by sufficiently mixing 5 parts of Compound A-1, 6 parts of Sorpol 3005X (surfactant, produced by Toho Chemical) and 89 parts of xylene.

Each of single use of an emulsion of Compound A-1, single use of a formulation of Flumioxazin (commercial name: Pledge, produced by Sumitomo Chemical, containing 50% of Flumioxazin), single use of a formulation of Sulfentrazone (commercial name: Authority, produced by Du Pont, containing 75% of Sulfentrazone), a mixed composition of an emulsion of Compound A-1 and a formulation of Flumioxazin, and a mixed composition of an emulsion of Compound A-1 and a solution of Sulfentrazone were diluted with water containing 1% Agri-dex (produced by Helena). Respective dilutions were uniformly sprayed from upper side onto foliages of broadleaf signalgrass grown as described above with a small sprayer such that the amounts of the active ingredients were the amounts shown in Table 4. Immediately after the treatment with the test compounds, seeds of soybean were sown.

After the treatment, they were raised in a greenhouse for 5 days and the effect against weeds was evaluated. In addition, after 14 days of the treatment, the phytotoxicity to soybean was evaluated. The results are shown in Table 4.

TABLE 4

| Test Compound | Amount of Active Ingredient (g/ha) | Herbicide Effect Broad signalgrass | Phytotoxicity Soybean |
|---|---|---|---|
| Compound A-1 | 5 | 2 | no |
| Compound A-1 | 20 | 4 | no |
| Flumioxazin | 100 | 1 | no |
| Flumioxazin | 600 | 3 | no |
| Sulfentrazone | 200 | 1 | no |
| Sulfentrazone | 1200 | 3 | no |
| Compound A-1 + Flumioxazin | 20 + 100 | 9 | no |
| Compound A-1 + Flumioxazin | 5 + 600 | 7 | no |
| Compound A-1 + Sulfentrazone | 20 + 200 | 9 | no |
| Compound A-1 + Sulfentrazone | 5 + 1200 | 7 | no |

Industrial Applicability

According to the present invention, weeds can be effectively controlled with a low dose. Particularly, in orchard and soybean field, weeds can be selectively controlled.

What is claimed is:

1. An herbicide composition comprising, as the active ingredients, a uracil compound represented by the following formula (I):

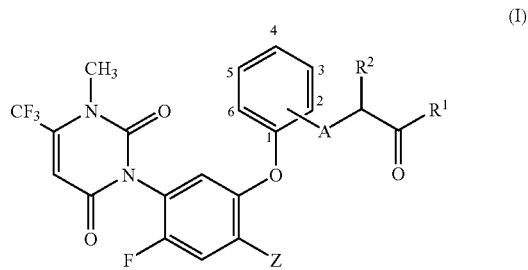

wherein Z represents a halogen atom or cyano; A represents an oxygen atom, a sulfur atom or NH; $R^1$ represents hydroxyl, C1–C7 alkoxy, C3–C7 alkenyloxy, C3–C7 alkynyloxy, C5–C7 cycloalkoxy, {(C1–C7 alkoxy)carbonyl}C1–C3 alkoxy, (C1–C7 alkylamino)oxy, {di(C1–C7 alkyl)amino}oxy, (C3–C7 alkylideneamino)oxy, C1–C7 alkylamino, di(C1–C7 alkyl)amino, C3–C7 alkenylamino, C3–C7 alkynylamino, C5–C7 cycloalkylamino, {(C1–C7 alkoxy)carbonyl}C1–C3 alkylamino or (C1–C7 alkoxy)amino, and $R^2$ represents a hydrogen atom or methyl, and N-(7-fluoro-3,4-dihydro-3-oxo-4-prop-2-ynyl-2H-1,4-benzoxazin-6-yl)cyclohex-1-ene-1,2-dicarboxamide.

2. The herbicide composition according to claim 1, wherein, in the uracil compound represented by the formula (I), A is an oxygen atom and $R^1$ is C1–C7 alkoxy.

3. The herbicide composition according to claim 1, wherein, in the uracil compound represented by the formula (I), the substituent represented by the following formula:

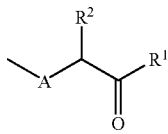

wherein $R^1$, $R^2$ and A represent the same meaning as above, is attached to the 2-position as defined in the formula (I).

4. The herbicide composition according to claim 1, wherein, in the uracil compound represented by the formula (I), Z is a halogen atom and $R^2$ is hydrogen.

5. The herbicide composition according to claim 1, wherein the mixing ratio of the uracil compound represented by the formula (I) to N-(7-fluoro-3,4-dihydro-3-oxo-4-prop-2-ynyl-2H-1,4-benzoxazin-6-yl)cyclohex-1-ene-1,2-dicarboxamide is 1:1 to 1:500 in weight ratio.

6. A method for controlling weeds comprising applying effective amounts of a uracil compound represented by the following formula (I):

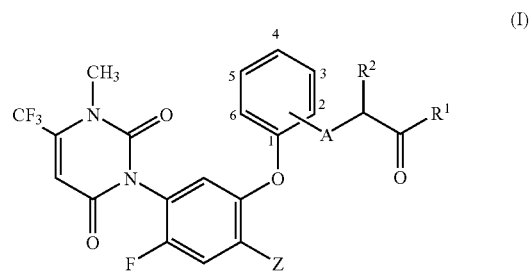

wherein Z represents a halogen atom or cyano; A represents an oxygen atom, a sulfur atom or NH; $R^1$ represents hydroxyl, C1–C7 alkoxy, C3–C7 alkenyloxy, C3–C7 alkynyloxy, C5–C7 cycloalkoxy, {(C1–C7 alkoxy)carbonyl}C1–C3 alkoxy, (C1–C7 alkylamino)oxy, {di(C1–C7 alkyl)amino}oxy, (C3–C7 alkylideneamino)oxy, C1–C7 alkylamino, di(C1–C7 alkyl)amino, C3–C7 alkenylamino, C3–C7 alkynylamino, C5–C7 cycloalkylamino, {(C1–C7 alkoxy)carbonyl}C1–C3 alkylamino or (C1–C7 alkoxy)amino, and $R_2$ represents a hydrogen atom or methyl, N-(7-fluoro-3,4-dihydro-3-oxo-4-prop-2-ynyl-2H-1,4-benzoxazin-6-yl)cyclohex-1-ene-1,2-dicarboxamide to weeds.

* * * * *